(12) United States Patent
Angeley et al.

(10) Patent No.: US 8,040,582 B2
(45) Date of Patent: Oct. 18, 2011

(54) LIGHT BEAM DELIVERY SYSTEM WITH POWER, WAVELENGTH AND SPOT SIZE CONTROL

(75) Inventors: David G. Angeley, Charlottesville, VA (US); Steven S. Christensen, Fremont, CA (US); Michael J. Simoneau, Morgan Hill, CA (US); Phillip H. Gooding, Mountain View, CA (US)

(73) Assignee: Topcon Medical Laser Systems, Inc., Santa Clara, CA (US)

( * ) Notice: Subject to any disclaimer, the term of this patent is extended or adjusted under 35 U.S.C. 154(b) by 476 days.

(21) Appl. No.: 12/253,076

(22) Filed: Oct. 16, 2008

(65) Prior Publication Data
US 2010/0097682 A1   Apr. 22, 2010

(51) Int. Cl.
*G02B 26/08* (2006.01)
(52) U.S. Cl. .................................................. 359/202.1
(58) Field of Classification Search ............... 359/202.1; 128/664, 665; 606/4
See application file for complete search history.

(56) References Cited

U.S. PATENT DOCUMENTS

| | | | |
|---|---|---|---|
| 4,917,486 A | 4/1990 | Raven et al. | |
| 5,400,176 A | 3/1995 | Dreessen et al. | |
| 5,612,673 A * | 3/1997 | Nunn | 340/471 |
| 5,713,364 A * | 2/1998 | DeBaryshe et al. | 359/561 |
| 6,099,522 A | 8/2000 | Knopp et al. | |
| 6,160,831 A | 12/2000 | Kleinschmidt et al. | |
| 7,146,983 B1 | 12/2006 | Hohla et al. | |
| 7,245,800 B1 | 7/2007 | Uhlhorn | |
| 2005/0286019 A1 | 12/2005 | Wiltberger et al. | |
| 2006/0100677 A1 | 5/2006 | Blumenkranz et al. | |
| 2006/0193592 A1 | 8/2006 | McNie et al. | |
| 2006/0197958 A1 | 9/2006 | Atia et al. | |
| 2007/0147730 A1 | 6/2007 | Wiltberger et al. | |
| 2007/0189664 A1 | 8/2007 | Andersen et al. | |

OTHER PUBLICATIONS

International Search Report and Written Opinion received for PCT Patent Application No. PCT/US2009/051583, mailed on Sep. 15, 2009, 9 pages.
International Preliminary Report on Patentability received for PCT Patent Application No. PCT/US2009/051583, issued on Apr. 19, 2011, 8 pages.

* cited by examiner

*Primary Examiner* — Euncha Cherry
(74) *Attorney, Agent, or Firm* — Morrison & Foerster LLP

(57) ABSTRACT

A beam delivery system for treating target tissue that includes an input for receiving a light beam, a variable attenuator for providing variable attenuation of the light beam, a power and wavelength detection assembly, a spot size adjustment assembly, and a controller. The power and wavelength detection assembly measures the power level of the beam, and detects when unwanted wavelengths are present in the light beam. The spot size adjustment assembly selectively feeds the beam through different optical fibers to achieve different spot sizes of the beam. The controller controls the variable attenuator, the power and wavelength detection assembly, and the spot size adjustment assembly to achieve the desired power and wavelength, and beam spot size.

20 Claims, 2 Drawing Sheets

LIGHT BEAM DELIVERY SYSTEM WITH POWER, WAVELENGTH AND SPOT SIZE CONTROL

FIELD OF THE INVENTION

The present invention relates to photomedical systems, and more particularly to a light based scanning photomedical system that can safely and reliably use different light sources with little or no control over the light source devices.

BACKGROUND OF THE INVENTION

Recently, light based scanning photomedical systems have been developed to accurately and efficiently treat tissue by automatically generating and applying patterns of light onto target tissue. For example, U.S. patent application publications 2005/0286019 and 2007/0147730 describe ophthalmic light beam pattern scanning devices that safely and efficiently scan a light beam in a predetermined pattern onto target tissue (e.g. in the patient's eye). The system allows the physician to align the light pattern to the target tissue, where the system automatically scans the light pattern onto the target tissue based upon a single activation by the physician. The application of light beam treatment using such a system can be accomplished far more quickly and accurately compared to earlier light beam systems that only allowed the physician to apply the light beam spots manually one at a time.

In such scanning photomedical systems, the light beam source is designed as an integral part of the scanning delivery system for several reasons. First, the control electronics for the system must have complete control over the operation of the light source in order to monitor and adjust the beam power, the beam activation, the beam wavelength, etc. Second, the optical elements used to receive, scan and deliver the light beam to the target tissue were designed integrally with the light source such that the desired spot size and pattern configuration could be achieved given the characteristics of the light beam (such as diameter, divergence, wavelength, etc.). Because these scanning systems are used for sensitive medical procedures such as ophthalmic photocoagulation, safety and reliability concerns and regulations dictate that the system have full control over the light source to ensure that the dosages and the locations of the light patterns are delivered safely and reliably.

It has recently become desirable to implement light-based scanning photomedical systems which utilize light sources external to the system, with little or no system control over the external light source. This would allow manufacturers of such photomedical systems to multi-source the suppliers of light sources. It would also provide users the ability to use existing light sources and/or swap light sources, for lower cost and greater flexibility. However, using light sources external to the photomedical system, with little or no control over the light source, compromises the integrity and reliability of existing scanning photomedical systems. There is a need for a scanning photomedical system that safely and reliably scans light beams onto the target tissue, where there is little or no control over the treatment light source by the photomedical system.

SUMMARY OF THE INVENTION

The aforementioned problems and needs are addressed by providing a beam delivery system for treating target tissue that includes an input for receiving a light beam, a plurality of optical elements for delivering the light beam from the input to target tissue, one or more pick-off optical elements for directing a first portion of the light beam to a first power detector for measuring a power level of the light beam first portion, and for directing a second portion of the light beam to a second power detector for measuring a power level of the light beam second portion, a first filter positioned to filter out or diffract certain wavelengths of light from the light beam first portion before reaching the first detector, and a controller for determining any difference between the power levels measured by the first and second detectors, and for taking a predetermined action if the determined difference exceeds a predetermined value.

The aforementioned problems and needs are also addressed by providing a beam delivery system that includes an input for receiving a light beam, a first scanning optical element for moving a direction of propagation of the light beam in a first direction and between a first position where the light beam impinges on a beam dump and a second position where the light beam is aligned to and passes through an aperture, and a second scanning optical element for selectively moving a direction of propagation of the light beam in a second direction between a plurality of positions, and a plurality of optical fibers each having their input ends disposed at one of the plurality of positions. The beam dump and the aperture are disposed between the first and second scanning optical elements.

The aforementioned problems and needs are further addressed by providing a beam delivery system that includes an input for receiving a light beam, a variable attenuator for providing variable attenuation of the light beam, a power and wavelength detection assembly, a spot size adjustment assembly, and a controller. The power and wavelength detection assembly includes one or more pick-off optical elements for directing a first portion of the light beam to a first power detector for measuring a power level of the light beam first portion, and for directing a second portion of the light beam to a second power detector for measuring a power level of the light beam second portion, and a first filter positioned to filter out or refract certain wavelengths of light from the light beam first portion before reaching the first detector. The spot size adjustment assembly includes a first scanning optical element for moving a direction of propagation of the light beam in a first direction and between a first position where the light beam impinges on a beam dump and a second position where the light beam is aligned to and passes through an aperture, a second scanning optical element for selectively moving a direction of propagation of the light beam in a second direction between a plurality of positions, wherein the beam dump and the aperture are disposed between the first and second scanning optical elements, a plurality of optical fibers each having their input ends disposed at one of the plurality of positions for selectively receiving the light beam, and a plurality of lenses disposed at output ends of the plurality of optical fibers for collimating the light beam exiting the output ends, wherein the plurality of optical fibers and the plurality of lenses are configured to produce different spot sizes of the light beam. The controller controls the variable attenuator, the power and wavelength detection assembly, and the spot size adjustment assembly, and is configured to determine a power level of the light beam using the power detectors, and adjust the variable attenuator in response to the determined power level, to determine any difference between the power levels measured by the first and second detectors, and take a predetermined action if the determined difference exceeds a predetermined value, to control the first scanning optical element to direct the light beam to the beam dump in a standby mode and through the aperture in a non-standby mode, and to control the second scanning optical element to direct the light beam to the input end of one of the optical fibers associated with a desired spot size.

Other objects and features of the present invention will become apparent by a review of the specification, claims and appended figures.

DETAILED DESCRIPTION OF THE PREFERRED EMBODIMENTS

The present invention is a light scanning delivery system that can accept the output of a light source, safely scan the light output onto the target tissue in the form of predetermined patterns, and do so safely and reliably with little or no control over the light source. The light scanning delivery system allows for the convenient selection and/or replacement of the light source, without having to reconfigure the delivery system or any electrical interface for light source control.

Figure 1:
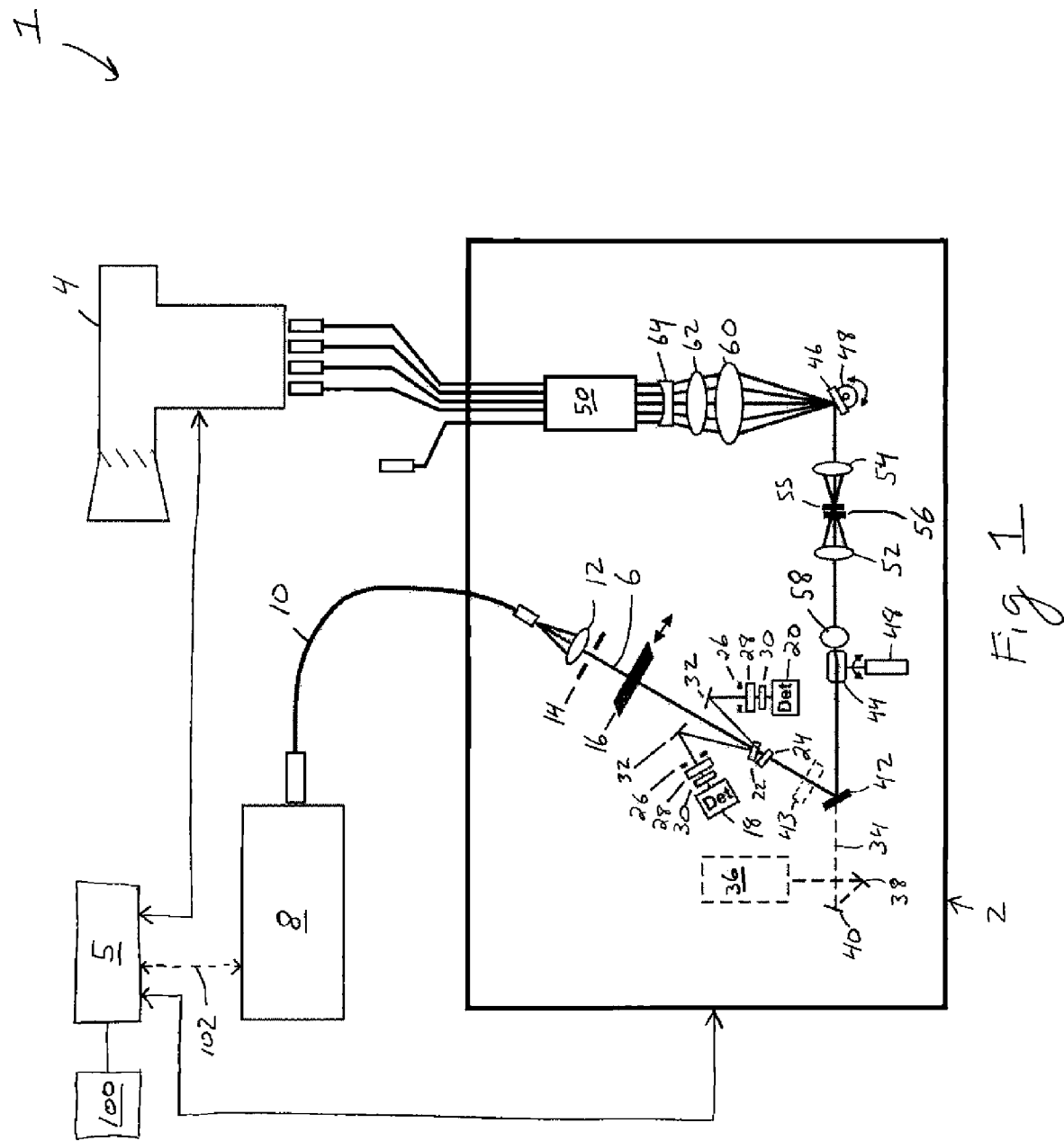
FIG. 1 is a schematic diagram of the light scanning delivery system.

The light scanning delivery system 1 is illustrated in FIG. 1, and includes a control module 2 and a scanning module 4, which are both operated under the control of a central controller 5. The light scanning delivery system 1 can operate using a treatment light beam 6 from any appropriate light source 8.

The light source 8 is preferably, but not necessarily, a laser. For the purposes of this disclosure, the light source 8 is preferably a commercially available ophthalmic laser system from a well known manufacturer such as Zeiss, Alcon or others, producing a light beam 6 having a suitable wavelength for the tissue being treated (e.g. 532 nm for ophthalmic photocoagulation of retinal tissue). However, a light beam produced by any appropriate light source for the medical procedure being conducted can be used.

The treatment light beam 6 is preferably delivered from the light source 8 to the control module 2 using an optical fiber 10 (e.g. a 50 μm core, 0.12 numerical aperture (NA) optical fiber). Alternately, the light beam 6 could be delivered through any other optical waveguide device or even through free-space propagation. The light beam 6 exits the optical fiber 10 and is directed through lens 12 to collimate the light beam 6, and through an aperture 14 to limit the NA of the light beam 6 to an acceptable limit for the scanning module 4. The collimated light beam 6 then travels through a variable attenuator 16 that is used to control the power of light beam 6 on the target tissue. The attenuation of the light beam 6 by attenuator 16 is preferably calibrated each time the system 1 is started, and the power level of the light beam 6 is monitored during operation by redundant optical power detectors 18/20 for safety and accuracy. Beam splitters 22/24 pick off a small amount of the light beam 6 and direct the picked off light to detectors 18/20. Apertures 26, neutral density filters 28 and diffusers 30 are preferably placed in front of detectors 18/20 to reduce directional sensitivity. Folding mirrors 32 are preferably used to direct the picked off light to detectors 18/20, so that beam splitters 22/24 can be oriented closer to orthogonal relative to light beam 6 thereby diminishing polarization effects for example.

Additionally, the beam splitters 22/24 are followed by a mirror 42. This mirror directs the beam towards the subsequent optical system but can also serve as a spectral filter. For example, mirror 42 can be a 532 nm high reflector HR. In this case, any wavelength other than the 532 nm treatment wavelength would be inefficiently reflected providing a further measure of safety.

A low power aiming beam 34 is combined into the light path of the light beam 6, to visually indicate the location of the treatment light beam 6 on the target tissue (either before or during the application of the treatment light beam 6 on the target tissue). An aiming beam light source 36 (e.g. laser diode at 635 nm) produces the aiming beam 34. Mirrors 38/40 (which are preferably adjustable) are used to direct the aiming beam 34 towards mirror 44. As shown in FIG. 1, the aiming beam can be combined passively using a combining mirror 42 (e.g. a dichroic mirror). Mirror 42 reflects light beam 6 and passes aiming beam 34, so that beams 6/34 precisely overlap. In order to project the aiming beam 34 onto the target tissue without the treatment light beam 6, the light source 8 can be deactivated or an optional shutter 43 can be used to selectively block light beam 6 anywhere before combining mirror 42.

Alternately, the aiming beam 34 can be co-aligned to the treatment beam path by switching mirror 44 (described below). Using an active combining method such as the switching or flip mirror avoids the complications of a passive dichroic technique when the wavelengths of the treatment and aiming beams are close or when it is difficult to obtain the desired efficient coating at both wavelengths. With this active combining method, aiming beam 34 bypasses mirror 42 (i.e. the aiming beam 36 goes around but not through mirror 42). The aiming beam 34 is coincident to the treatment path after mirror 44 when the mirror 44 is properly oriented. The aiming and treatment beams 6/34 can be switched as a function of time.

The light beams 6/34 then encounter orthogonal scanning mirrors 44/46, which rotate to move the propagation of the beams 6/34 in near-orthogonal directions. Galvanometers 48 are preferably used to rotate the positions of scanning mirrors 44/46, however, any appropriate motor or other optical element moving device can be used to rotate scanning mirrors 44/46 in orthogonal directions. One or both of scanning mirrors 44/46 are used to selectively direct the beams 6/34 into one of a plurality of optical fibers in optical fiber bundle 50. While optical fiber bundle 50 is shown to contain 5 separate optical fibers, additional or few optical fibers could be included in fiber bundle 50.

A pair of lenses 52/54 are disposed between scanning mirrors 44/46, to produce an image relay system whereby the image conjugates are mirrors 44 and 46. In general, for collimated light, lenses 52/54 form a near-afocal relay system with near-unity magnification. An aperture 55, positioned between lenses 52/54, is imaged onto the face of the optical fiber bundle 50, to assure alignment of the beams 6/34 thereto and to allow a constant window for the spot in the direction in which scanning mirror 44 moves. A beam dump 56 is also positioned between lenses 52/54, to provide a safe location to "park" the beams 6/34 when not being delivered to the target tissue (i.e. moving the mirror 44 to direct the beams 6/34 to beam dump 56 acts as a shutter for all downstream optical components and the target tissue). Since the beam dump 56 is after the power detectors 18/20, the treatment beam 6 can be activated during calibration and self-test operations without risk of the beam reaching the patient. While the aperture 55 and beam dump 56 are shown as separate components, they can also be combined into a single element (e.g. a plate with an aperture hole that can sustain and block the full power of the beams 6/34 when not aligned to the aperture hole). An optional adjustable mirror 58 can also be placed between scanning mirrors 44/46 to aid in system alignment.

Lenses 60, 62 and 64 form a lens system for focusing the beams 6/34 into the various optical fibers of the fiber bundle 50. These lenses create a telecentric flat field input for the fiber bundle 50 to assure optimum transmission at the intrinsic NA, core size, and focal placement of the optical fibers. Preferably, the input ends of the optical fibers are arranged in a linear manner that matches the direction of movement of scanning mirror 46. With this configuration, scanning mirror 44 can be used to either direct the beams 6/34 to the beam dump 56 or through the aperture 55 and on to the optical fiber bundle 50 (and perform fine adjustment alignment to the optical fiber input ends), and scanning mirror 46 can be used to select the particular optical fiber of fiber bundle 50 to receive the beams 6/34 by aligning them to the input end of that optical fiber.

Figure 2:
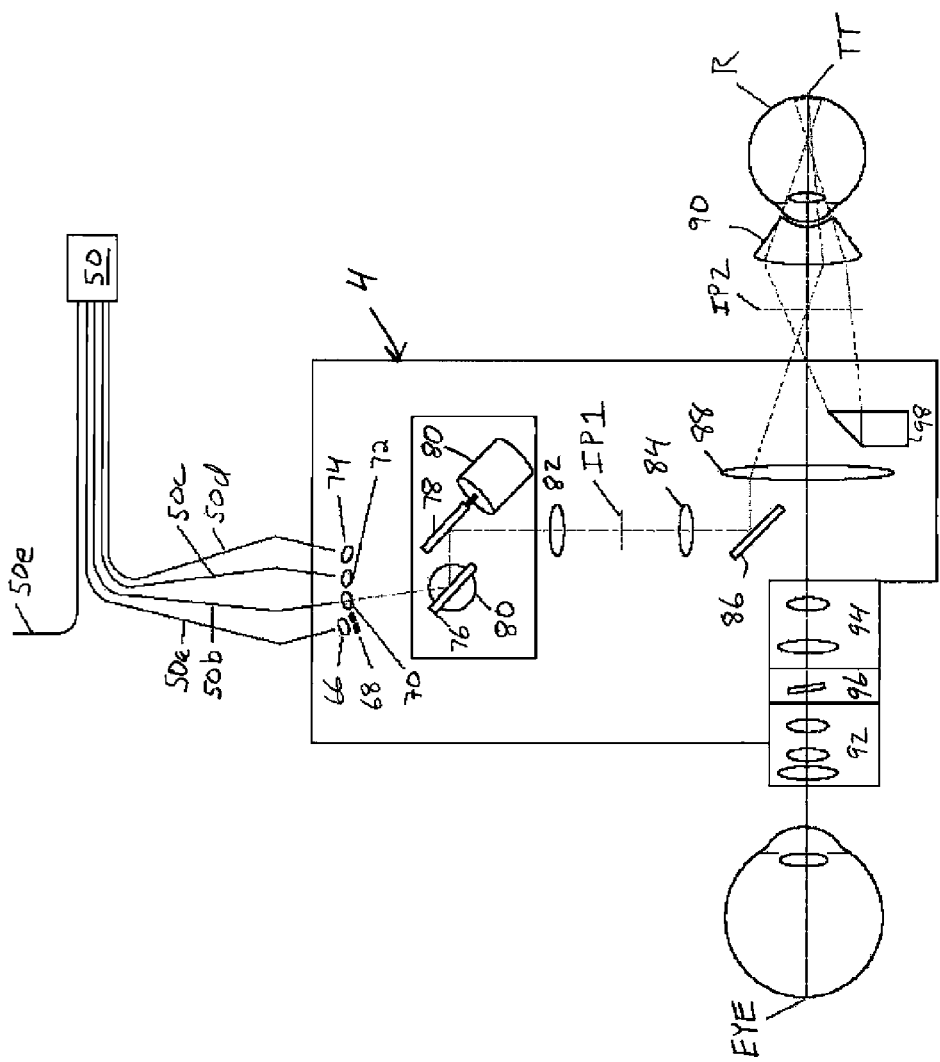
FIG. 2 is a schematic diagram of the scanning module of the light scanning delivery system.

FIG. 2 illustrates the components of the scanning module 4. In the configuration shown, fiber bundle 50 includes four optical fibers 50*a*, 50*b*, 50*c*, and 50*d* for selectively transmitting beams 6/34 to the scanning module 4. Each optical fiber 50*a-d* preferably has a dedicated lens configuration at it's output end to condition the exiting light beams 6/34 for delivery to the patient. Preferably, each fiber/lens configuration provides a different spot size at the target tissue, so that different spot sizes can be selected by selecting which fiber 50*a-d* is used to deliver the beams 6-34 to the scanning module 4. Specifically, when light beams 6/34 are exiting from fiber 50*a*, they encounter lens 66 (which serves to collimate the beams 6/34) and aperture 68 (which serves to reduce the numerical aperture by obscuring all but the central portion of the beam 6/34). Likewise, when the light beams 6/34 are exiting from optical fibers 50*b*, 50*c* or 50*d*, they are conditioned by lenses 70, 72 or 74 respectively. To achieve different spot sizes, optical fibers 50*a* and 50*b* may have the same core diameter but the focusing properties of lenses 66 and 70 differ. Likewise, lenses 72/74 can have the same focusing properties, but optical fibers 50*c* and 50*d* may have different core diameters (to produce different spot sizes but with the same numerical aperture). By selecting spot size in this manner, the cone angle of the light is not altered. Additionally, a greater margin of safety is achieved as opposed to traditional zoom or turret systems, where the product of the spot diameter and the cone angle is varied (a.k.a. "The Lagrange Invariant" is different for each spot size). In this way, the large spot sizes can still have relatively steep cone angles forming a small region of concentrated light (i.e. the Rayleigh range is small even for large spot sizes). An additional optical fiber 50*e* may be included in the fiber bundle 50 which can be used to provide light beams 6/34 to an endoprobe or laser indirect ophthalmoscope (not shown).

The output of each optical fiber 50*a-d* (and the associated light conditioning optics thereof) is directed to another set of orthogonal scanning mirrors 76/78, which are rotated by galvanometers 80 in orthogonal directions. The first scanning mirror 76 can be rotated to redirect the light beams 6/34 from a given one of the optical fibers 50*a-d* into the remainder of the optical delivery system. This "selects" that optical fiber, and does not permit light from other optical fibers to propagate through the rest of the system. Because optical fibers 50*a-d* are physically separated and pointed in different directions, scanning mirror 76 must be rotated into position to intercept the light beams 6/34 from the selected fiber and transmit them to scanning mirror 78. This configuration has the added benefit of reducing any stray light that may be delivered by the non-selected optical fibers, as the light from optical fibers other than that which is selected will not propagate in a manner that exits the system to reach the target tissue. In addition to selecting the output from the selected optical fiber, scanning mirrors 76/78 create the scanned 2-dimensional pattern for projection onto the target tissue. The pattern can comprise a single spot, a plurality of separate spots (in the case of a pulsed light source) or one or more straight or curved lines or line segments (in the case of a continuous light source). Again, galvanometers 80 can be replaced by any appropriate motor or other optical element moving device that can be used to rotate scanning mirrors 76/78 in orthogonal directions.

The pattern of scanned light from the scanning mirrors 76/78 is delivered to the target tissue by lenses 82, 84, mirror 86, lens 88 and ophthalmic lens 90. Lens 82 serves to create an intermediate scanned pattern at image plane IP1. Lens 84 further conditions the pattern for focusing by lens 88 (which is preferably an infinity-corrected microscope objective lens) via the ophthalmic lens 90 (which can be a contact lens used to create an intermediate image of the target tissue at an image plane IP2). Mirror 86 is used to fold the optical path. Lens 88 serves to both focus the scanned pattern and provide the microscope image for viewing the target tissue by the physician. In the example shown, the target tissue TT is the retina R of a patient's eye, and is imaged through or around folding mirror 86.

The scanning module 4 preferably includes a slit lamp microscope assembly for reviewing the target tissue. The slit lamp microscope assembly includes binocular and tube lens optics 92 (for magnifying the image of the target tissue as viewed through lens 88 and through or around mirror 86), magnification changing optics 94 (that allow the user to adjust the magnification of the image) and an eye safety filter 96 (to assure that no potentially harmful levels of light from the treatment beam 6 enter the user's eye (EYE)). The eye safety filter 96 is preferably color-balanced to provide for a photopically neutral transmission and clear visibility of the aiming beam pattern on the target tissue. An illumination source 98 provides illumination light to better visualize the target tissue.

The central controller 5 is used to monitor and control the various components of control and scanning modules 2/4. Specifically, the controller 5 monitors the power of light beam 6 using detectors 18/20, and controls the movement of variable attenuator 16 to achieve the desired power level of beam 6. If light source 8 is capable of producing multiple wavelengths of light, the detectors 18/20 can be configured to verify that the intended wavelength is being produced by the light source 8. Specifically, assuming that the desired wavelength is 532 nm, filter 28 for detector 18 could be configured to filter out other wavelengths of light (i.e. simply pass just 532 nm light while attenuating other wavelengths), while filter 28 for detector 20 would be a neutral density filter that does not selectively filter out other wavelengths of light. Alternately, folding mirror 32 for detector 18 could further be a diffractive element that separates the various wavelengths such that only the 532 nm light is aligned to the detector 18 (i.e. effectively filters out other wavelengths from the beam via misalignment), such that diffractive element 32 acts as the wavelength filter. With this configuration, the controller 5 can automatically detect if wavelengths other than the desired 532 rim wavelength are present in beam 6, because that would result in a significant discrepancy between the detected power levels by detectors 18 and 20. The controller 5 can then indicate a fault condition if improper wavelengths are detected, or can take some other action (e.g. change the display to read the detected wavelength, adjust the optical system to accommodate the different wavelength and deliver the requested spot diameter, change the set or range of available spot diameters, etc.). Filter 28 can be configured for easy replacement with other filters for other wavelengths, or can include a plurality of different wavelength filters (e.g. on a rotatable filter wheel optionally under the control of controller 5), so that this detector scheme can be used to verify operation at one of a number of different desired wavelengths. Filter 30 can also have non-uniform wavelength filtering characteristics and still be used to help detect undesired wavelengths, so long as it has wavelength filtering characteristics that differ from that of filter 28.

The controller 5 controls the operation of the aiming beam light source 36, and also controls the position of scanning mirror 44 to either park the beams 6/34 on the beam dump 56 or position the beams 6/34 to pass through aperture 55. The position of scanning mirror 46 is also controlled by controller 5, to select which optical fiber in bundle 50 delivers the beams 6/34 to the scanning module 4 (and thus what spot size will be used for the medical procedure). Finally, controller 5 also controls the scanning mirrors 76/78 to generate the desired beam pattern that will be projected onto the target tissue.

The controller 5 operates the system in response to a user interface 100, which allows the user to select the system's operating parameters that are desired for the particular procedure being conducted, including the specific pattern configuration (size, number and positioning of spots or line segments forming the pattern, etc.), the power of the treatment beam 6 and aiming beam 34, confirmation of the desired wavelength, the exposure time, the number of applications or patterns to be used, etc. The user interface 100 can include a control console with dedicated buttons and a display, and/or a touch screen display with soft button control. The user interface can also include a treatment activation device, such as a footswitch, to trigger the application of the pattern of treatment light once the alignment, power, wavelength, and spot size has been set and confirmed.

With the light scanning delivery system 1 described above, there need be only one connection with an otherwise generic light source 8: the optical connection (e.g. optical fiber 10) delivering the treatment light beam 6. Without any additional input from or control over the light source 8, the system 1 can verify the proper wavelength, set the desired power, block the treatment beam 6 until ready for use, set the desired spot size, generate and project the aiming pattern (to enable and confirm alignment), and generate and project the treatment pattern aligned to the aiming pattern, all while adhering to the same safety and reliability standards as those for scanning systems that are integrally designed with and have complete control over a dedicated treatment scheme light source. Because the system 1 can operate independently from the light source 8, the light source 8 can be supplied separate from system 1. Moreover, the light source 8 can be exchanged with one having different optical properties and a different control interface, without requiring the system 1 to be compatible with any aspect of the control interface or electrical output from the new light source.

While system 1 is ideal for use with a light source 8 using a single connection therebetween (optical fiber 10), it is also possible for the system 1 to have additional connection(s) 102 with the light source 8. For example, many light source devices have an interlock system that shuts down the light source should the interlock system be tripped (indicating a safety issue has arisen such as a cover is open or a condition exists making the production of light output unsafe). Controller 5 can be connected to the interlock system of the light source 8, so that the light source 8 can be immediately deactivated should the controller 5 determine a safety issue as arisen (i.e. a cover of system 1 is opened). Additionally, many light source devices have a trigger input, whereby the output of light beam 6 from light source 8 can be remotely activated or deactivated using the trigger input. Controller 5 can be connected to the trigger input to activate the output of beam 6 from light source 8 (e.g. when the beam block 56 is used while confirming power and wavelength in a standby mode, or when the beam 6 is to be applied to the target tissue after alignment has been confirmed), and to deactivate the output of beam 6 from light source 8 during a standby mode (e.g. during system alignment using aiming beam 34). Should the controller 5 be connected to the trigger input to control the activation and deactivation of light source 8, then shutter 43 could be omitted. No matter which connection configuration is used, the system 1 provides complete and safe control over the alignment and application of light patterns on the target tissue, with little or no control over the treatment light source 8.

It is to be understood that the present invention is not limited to the embodiment(s) described above and illustrated herein, but encompasses any and all variations falling within the scope of the appended claims. For example, while beam propagation movements are described above are implemented by rotating mirrors, one skilled in the art would appreciate that other techniques for beam propagation movements can be utilized instead, such as translating non-planar mirror or lenses, using one or more rotating wedges, using a two-dimensional acousto-optic deflector, etc. Further, references to "the present invention" or "the invention", etc. herein are not intended to limit the scope of any claim or claim term, but instead merely make reference to one or more features that may be covered by one or more of the claims.

What is claimed is:

1. A beam delivery system for treating target tissue comprising:
   an input for receiving a light beam;
   a plurality of optical elements for delivering the light beam from the input to target tissue;
   one or more pick-off optical elements for directing a first portion of the light beam to a first power detector for measuring a power level of the light beam first portion and for directing a second portion of the light beam to a second power detector for measuring a power level of the light beam second portion;
   a first filter positioned to filter out or diffract certain wavelengths of light from the light beam first portion before reaching the first detector; and
   a controller for determining any difference between the power levels measured by the first and second detectors, and for taking a predetermined action if the determined difference exceeds a predetermined value.

2. The beam delivery system of claim 1, wherein the input is an output end of an optical fiber.

3. The beam delivery system of claim 1, wherein the one or more pick-off optical elements comprise:
   a first beam splitter disposed in the light beam for extracting the first portion from the light beam by reflection; and
   a second beam splitter disposed in the light beam for extracting the second portion from the light beam by reflection.

4. The beam delivery system of claim 1, further comprising:
   a second filter positioned to filter the light beam second portion before reaching the second detector, wherein the second filter has different wavelength filtering characteristics from that of the first filter.

5. The beam delivery system of claim 1, further comprising:
 a first aperture plate defining a first aperture aligned to the light beam first portion;
 a first diffuser aligned to the light beam first portion;
 a second aperture plate defining a second aperture aligned to the light beam first portion; and
 a second diffuser aligned to the light beam second portion.

6. The beam delivery system of claim 1, further comprising:
 a variable attenuator disposed in the light beam before the light beam reaches the one or more pick-off optical elements.

7. The beam delivery system of claim 1, wherein the first filter comprises different portions thereof with differing wavelength filtering characteristics, and wherein the controller is configured to selectively place the different portions of the first filter in the light beam first portion.

8. The beam delivery system of claim 1, wherein the first filter attenuates the certain wavelengths from the first light beam.

9. The beam delivery system of claim 1, wherein the first filter diffracts the certain wavelengths from the first light beam.

10. The beam delivery system of claim 1, wherein the predetermined action is an indication of a fault condition.

11. A beam delivery system, comprising:
 an input for receiving a light beam;
 a variable attenuator for providing variable attenuation of the light beam;
 a power and wavelength detection assembly, comprising:
  one or more pick-off optical elements for directing a first portion of the light beam to a first power detector for measuring a power level of the light beam first portion, and for directing a second portion of the light beam to a second power detector for measuring a power level of the light beam second portion,
  a first filter positioned to filter out or refract certain wavelengths of light from the light beam first portion before reaching the first detector;
 a spot size adjustment assembly, comprising:
 a first scanning optical element for moving a direction of propagation of the light beam in a first direction and between a first position where the light beam impinges on a beam dump and a second position where the light beam is aligned to and passes through an aperture,
 a second scanning optical element for selectively moving a direction of propagation of the light beam in a second direction between a plurality of positions, wherein the beam dump and the aperture are disposed between the first and second scanning optical elements,
 a plurality of optical fibers each having their input ends disposed at one of the plurality of positions for selectively receiving the light beam, and
 a plurality of lenses disposed at output ends of the plurality of optical fibers for collimating the light beam exiting the output ends, wherein the plurality of optical fibers and the plurality of lenses are configured to produce different spot sizes of the light beam; and
 a controller for controlling the variable attenuator, the power and wavelength detection assembly, and the spot size adjustment assembly, wherein the controller is configured to:
  determine a power level of the light beam using the power detectors, and adjust the variable attenuator in response to the determined power level,
  determine any difference between the power levels measured by the first and second detectors, and take a predetermined action if the determined difference exceeds a predetermined value,
  control the first scanning optical element to direct the light beam to the beam dump in a standby mode and through the aperture in a non-standby mode, and
  control the second scanning optical element to direct the light beam to the input end of one of the optical fibers associated with a desired spot size.

12. The beam delivery system of claim 11, wherein the one or more pick-off optical elements comprise:
 a first beam splitter disposed in the light beam for extracting the first portion from the light beam by reflection; and
 a second beam splitter disposed in the light beam for extracting the second portion from the light beam by reflection.

13. The beam delivery system of claim 11, further comprising:
 a second filter positioned to filter or diffract the light beam second portion before reaching the second detector, wherein the second filter has different wavelength filtering characteristics from that of the first filter.

14. The beam delivery system of claim 11, wherein the first filter comprises different portions thereof with differing wavelength filtering characteristics, and wherein the controller is configured to selectively place the different portions of the first filter in the light beam first portion.

15. The beam delivery system of claim 11, further comprising:
 a first aperture plate defining a first aperture aligned to the light beam first portion;
 a first diffuser aligned to the light beam first portion;
 a second aperture plate defining a second aperture aligned to the light beam first portion; and
 a second diffuser aligned to the light beam second portion.

16. The beam delivery system of claim 11, wherein the beam dump and the aperture are integrally formed as a single device.

17. The beam delivery system of claim 11, wherein the first direction is orthogonal to the second direction.

18. The beam delivery system of claim 11, wherein the plurality of positions are disposed along a single line.

19. The beam delivery system of claim 11, wherein the single line extends parallel to the second direction.

20. The beam delivery system of claim 11, wherein the predetermined action is an indication of a fault condition.

* * * * *